(12) United States Patent
Dasgupta et al.

(10) Patent No.: US 6,833,254 B2
(45) Date of Patent: Dec. 21, 2004

(54) METHOD TO IDENTIFY IRES ELEMENTS

(75) Inventors: Asim Dasgupta, Los Angeles, CA (US); Arun Venkatesan, Los Angeles, CA (US)

(73) Assignee: The Regents Of The University Of California, Oakland, CA (US)

( * ) Notice: Subject to any disclaimer, the term of this patent is extended or adjusted under 35 U.S.C. 154(b) by 0 days.

(21) Appl. No.: 10/087,171

(22) Filed: Mar. 1, 2002

(65) Prior Publication Data

US 2002/0187497 A1 Dec. 12, 2002

Related U.S. Application Data

(60) Provisional application No. 60/272,755, filed on Mar. 1, 2001.

(51) Int. Cl.[7] .......................... C12P 21/06; C12Q 1/68; C12Q 1/06; C12N 5/06; C12N 15/00
(52) U.S. Cl. ............................ 435/69.1; 435/6; 435/39; 435/334; 435/320.1
(58) Field of Search ........................... 435/6, 39, 69.1, 435/334, 320.1

(56) References Cited

U.S. PATENT DOCUMENTS 6,171,821 B1    1/2001   Korneluk et al. .......... 435/69.1

OTHER PUBLICATIONS

Agol et al. "Prokaryotic–like Cis Elements in the Cap–Independent Internal Initiation of Translation on Picornavirus RNA" Cell 68:119–131 (1992).

Chappell et al. "A 9–nt Segment of a Cellular mRNA Can Function As an Internal Ribosome Entry Site (IRES) and When Present in Linked Multiple Copies Greatly Enhances IRES Activity" Proc. Natl. Acad. Sci. USA 97(4):1536–1541 (2000).

Fukushi et al. "Specific Interaction of a 25–Kilodalton Cellular Protein, a 40S Ribosomal Subunit Protein, with th Internal Ribosomal Entry Site of Hepatitis C Virus Genome" Virus Genes 19(2):153–161 (1999).

Honda et al. "A Phylogenetically Conserved Stem–Loop Structure at the 5' Border of the Internal Ribosome Entry Site of Hepatitis C Virus Is Required for Cap–Independent Viral Translation" J. Virol. 73(2):1165–1174 (1999).

Jackson et al. "Internal Initiation of Translation in Eukaryotes: The Picornavirus Paradigm and Beyond" RNA 1:985–1000 (1995).

Johannes et al. "Cap–Independent Polysomal Association of Natural mRNAs Encoding c–myc, BiP, and eIF4G Conferred by Internal Ribosome Entry Sites" RNA 4:1500–1513 (1998).

Kolupaeva et al. "Ribosomal Binding to the Internal Ribosomal Entry Site of Classical Swine Fever Virus" RNA Society 6:1791–1807 (2000).

Nanbru et al. "Alternative Translation of the Proto–oncogene c–myc by an Internal Ribosome Entry Site" Journal of Biological Chemistry 272(51):32061–32066 (1997).

Ohlmann et al. "An Internal Ribosome Entry Segment Promotes Translation of the Simian Immunodeficiency Virus Genomic RNA" Journal of Biological Chemistry 275(16):11899–11906.

(List continued on next page.)

*Primary Examiner*—Hankyel T. Park
(74) *Attorney, Agent, or Firm*—Morrison & Foerster LLP

(57) ABSTRACT

A method to identify internal ribosome entry site (IRES) elements using a bicistronic expression system for reporter proteins is described. The IRES elements thus identified are useful in identifying trans-acting translation factors and as antiviral agents.

14 Claims, 11 Drawing Sheets

OTHER PUBLICATIONS

Owens et al. "Identification of Two Short Internal Ribosome Entry Sites Selected from Libraries of Random Oligonucleotides" PNAS 98(4):1471–1476 (2001).

Pestova et al. "Functional Dissection of Eukaryotic Initiation Factor 4F: the 4A Subunit and the Central Domain of the 4G Subunit Are Sufficient to Mediate Internal Entry of 43S Preinitiation Complexes" Molecular and Cellular Biology 16(12):6870–6878 (1996).

Pestova et al. "A Prokaryotic–like Mode of Cytoplasmic Eukaryotic Ribosome Binding to the Initiation Codon During Internal Translation Initiation of Hepatitis C and Classical Swine Fever Virus RNAs" Genes & Development 12:67–83 (1998).

Robertson et al. "A Selection System for Functional Internal Ribosome Entry Site (IRES) Elements: Analysis of the Requirement for a Conserved GNRA Tetraloop in the Encephalomyocarditis Virus IRES" RNA 5:1167–1179 (1999).

Tsukiyama–Kohara et al. "Internal Ribosome Entry Site Within Hepatitis C Virus RNA" Journal of Virology 66(3):1476–1483 (1992).

Wang et al. "Translation of Human Hepatitis C Virus RNA in Cultured Cells Is Mediated by an Internal Ribosome-–Binding Mechanism" J. Virol. 67:3338–3344 (1993).

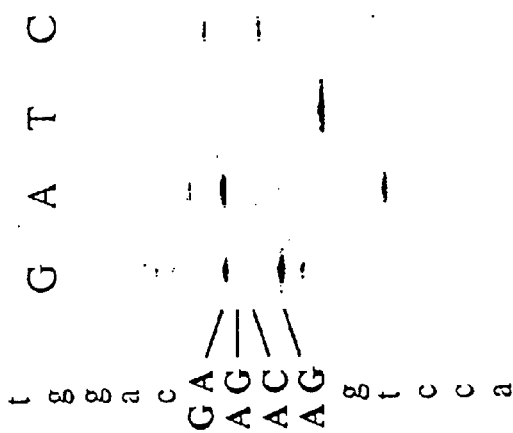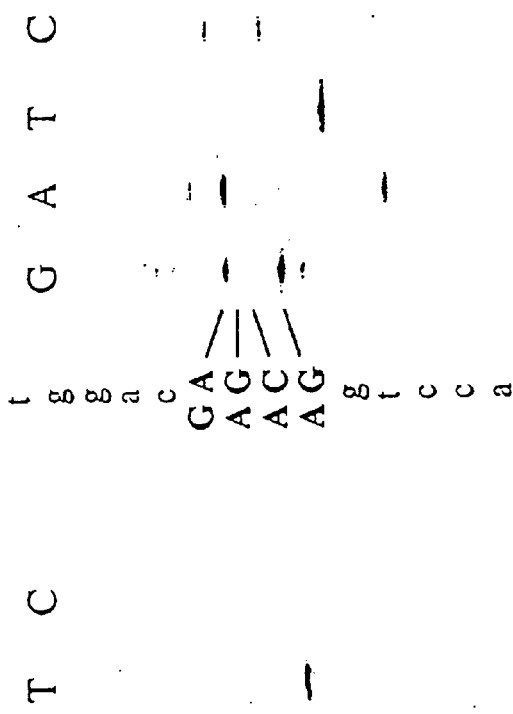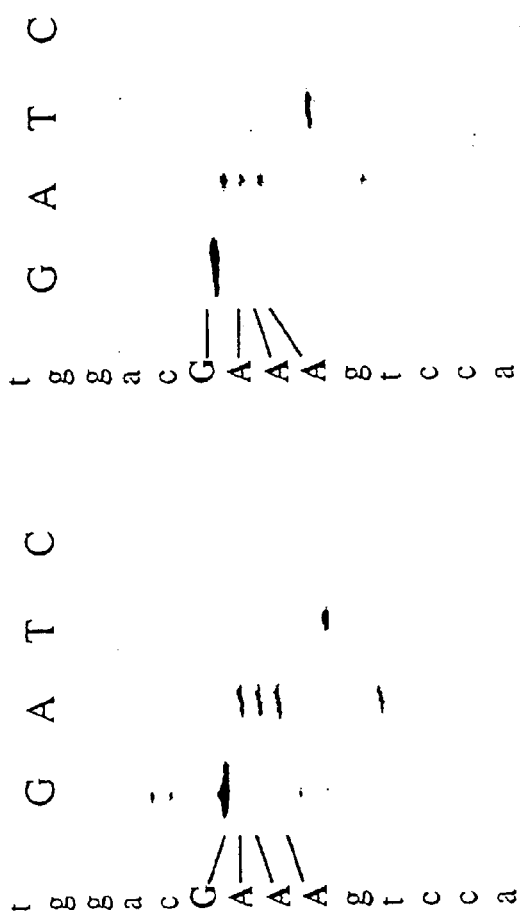
Figure 2B-3
Figure 2B-2
Figure 2B-1

| Name | Sequence (SEQ ID NOS: 1-5) |
|---|---|
| PS1 | 5' CACAgTACgTAAgCTTAAgCTAgATAAgggTATATTTTgCg 3' |
| PS2 | 5' gAAATAgCTATCCTCCATCACTgCACCgagACTACggTTgCgCgTgTCgT 3' |
| PS3 | 5' TgACAAACTgTACATgCCgTTAACTgTAATTTTgCgTgATTTTTTgTAg 3' |
| PS4 | 5' AggTggTAgCCgCAAACATAgTTCAATACAAACTgCTgTCTCggCgg 3' |
| PS5 | 5' AggCAgTATAATCAgTTCCCACATAgAAAACCAggACTgTATCAAAgTgT 3' |

Figure 2C

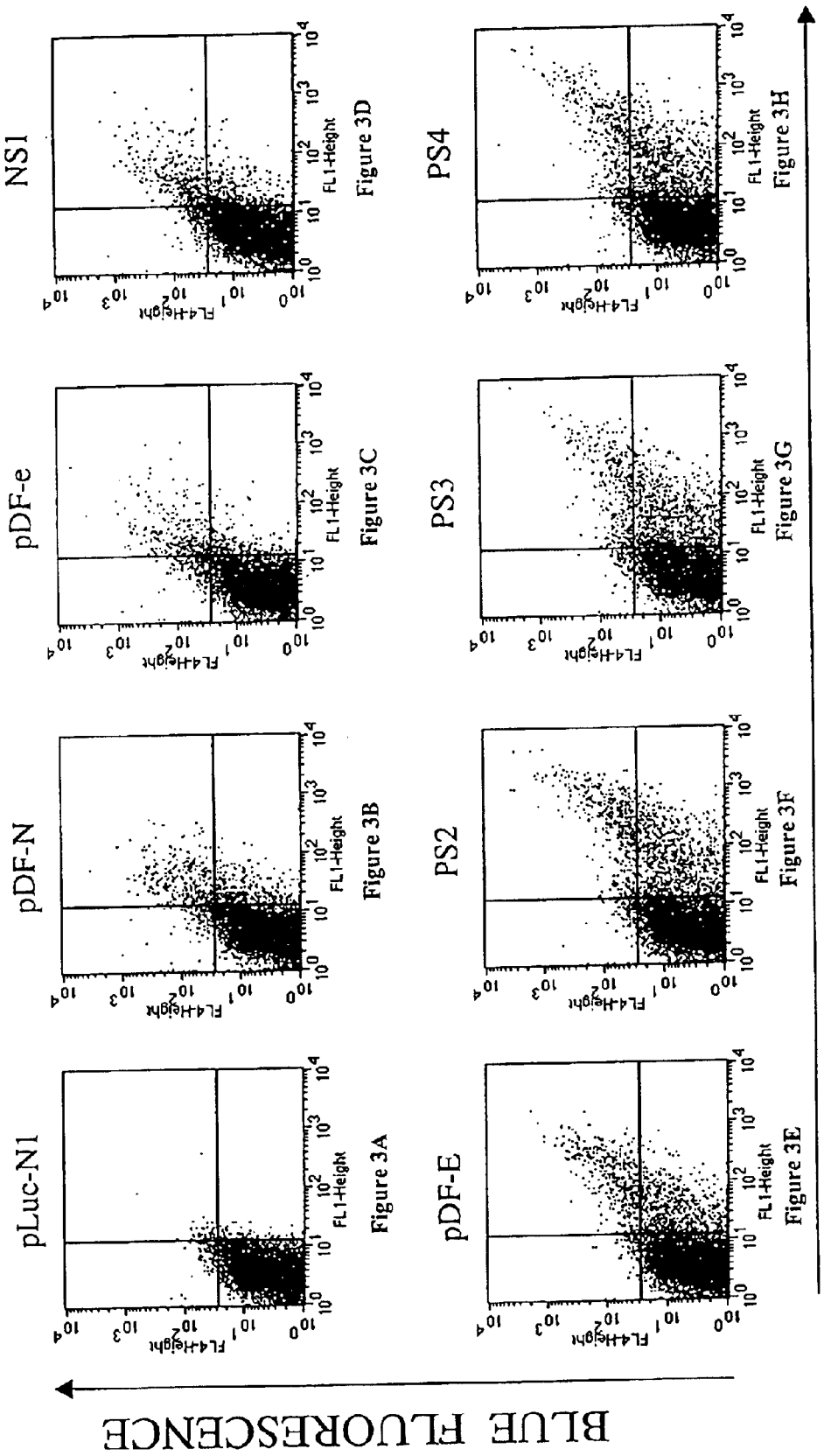

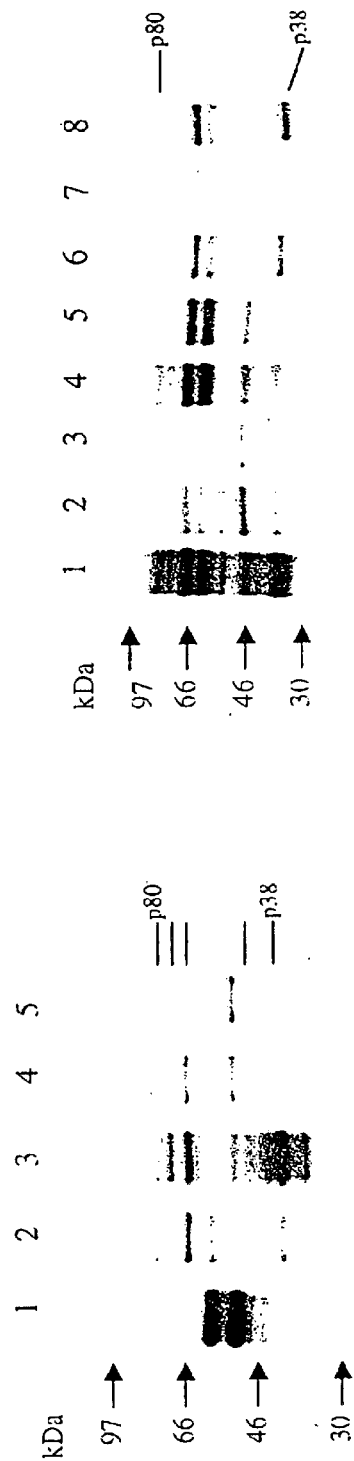
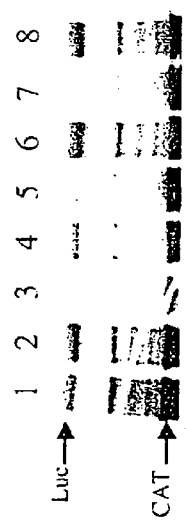
Figure 5A
Figure 5B
Figure 5C

METHOD TO IDENTIFY IRES ELEMENTS

CROSS-REFERENCE TO RELATED APPLICATIONS

This application claims priority under 35 U.S.C. §119(e) to provisional application No. 60/272,755 filed 1, Mar. 2001. The contents of this application are incorporated herein by reference in their entirety.

TECHNICAL FIELD

The invention relates to methods to determine whether a particular nucleotide sequence represents an element which behaves as an internal ribosome entry site (IRES). More specifically, the invention employs a bicistronic system involving both cap-mediated and IRES mediated translation.

BACKGROUND ART

Translation of cellular mRNA is generally mediated by a "cap" at the 5' end of mRNA upstream of the coding sequence in the untranslated region which is responsible for interaction of the messenger RNA with the ribosome. However, certain viruses, including picornaviruses, rhinovirus and HCV have been shown to possess an upstream region, designated IRES, which mediates translation in the absence of the cap structure at the 5' end of the messenger RNA. This IRES region is typically at least 450 nucleotides long when it occurs in viruses and possesses, at its 3' end, a conserved UUUC motif followed by a polypyrimidine tract, a G-poor spacer and an AUG triplet. Agol, V., et al., *Cell* (1992) 68:119–131. The IRES is located within the 5' untranslated (5' UTR) region, but downstream from the cap. Certain cellular mRNA's, such as those encoding BiP, c-myc, and eIF4G also contain IRES elements. Johannes, G., et al., *RNA* (1998) 4:1500–1513, Tsukiyama-Kohara, K., et al., *J. Virol.* (1992) 66:1476–1483; and Wang, C., et al., *J. Virol.* (1993) 67:3338–3344.

While viral IRES elements do not require the cap binding protein for complex formation, various other portions of the protein are required for some viral-derived sequences. Pestova, T. V., et al., *Genes Dev.* (1998) 12:67–83; and Pestova, T. V., et al., *Mol. Cell. Biol.* (1996) 16:6870–6878. Other trans-acting factors, such as La, PTB, PCBP2, and unr have been shown to interact with viral IRES elements.

The mechanism whereby these IRES elements assist in mediating translation is not known. Little, if any, sequence homology has been found between the various IRES elements (Jackson, R. J., et al., *RNA* (1995) 1:985–1000). RNA secondary structure appears to play an important role in viral IRES-mediated translation. For example, phenotypic revertants of point mutations in picornaviral IRES elements often include second-site suppressor mutations that restore the wild-type base pairing, suggesting that maintenance of RNA structure is crucial for IRES activity. Also, maintenance of a phylogenetically conserved stem-loop structure was found to be important for the ability of the HCV IRES to mediate translation (Honda, M., et al., *J. Virol.* (1999) 73:1165–1174). Thus, both sequence and structure are important in viral IRES-mediated translation.

Little is known regarding the cis-acting requirements of cellular IRES elements. It has been proposed that a number of cellular IRES elements possess a Y-type stem-loop-structure, but the ability of these RNA's to mediate translation has not been correlated with maintenance of the Y-shaped structure. Many of the studies investigating cis-acting requirements for IRES elements have focused on mutational analysis of viral 5'UTR's. However, the 5' regions of viral RNA's are involved in other functions crucial for the viral life cycle, including replication and packaging and cis-acting signals for different viral functions overlap in the 5' UTR, making it difficult to identify a viral sequence that is solely responsible for IRES-mediated translation.

Recently, the 196 nucleotide 5' UTR of the mouse Gtx mRNA was found to contain a 9 nucleotide segment that can function as an IRES element. Because this stretch of 9 nucleotides is complementary to 18S rRNA, it was suggested that IRES activity was due to the ability of the 9 nucleotide segment to base-pair with rRNA, thereby recruiting the ribosome to the RNA (Chappell, S. A., et al., *Proc. Natl. Acad. Sci. USA* (2000) 97:1536–1541). However, comparisons of other IRES elements with rRNA sequences have not, as yet, revealed regions of obvious complementarity.

Robertson, M. E. M., et al., *RNA* (1999) report an IRES selection system using a cell surface-expressed epitope whose expression is selected for by antibody-coated magnetic beads. A four-base region of the EMCV IRES, proposed to form a GNRA tetraloop, was randomized to a 256 member library and transfected into COS-7 cells. The sequence RNRA was identified as being optimal for translation activity. After three rounds of selection, a maximum of 10–20% of selected clones contained strong IRES elements. At a minimum, the initial library contained 16 positive elements (representing all combinations of the sequence RNRA) out of 256 total elements, thus, at most, a 3-fold increase (from 6% to 20%) in desirable IRES elements was achieved after three rounds of screening.

DISCLOSURE OF THE INVENTION

It has now been shown that although, for example, the native IRES elements contain hundreds of nucleotides, IRES activity can be demonstrated by relatively small segments of RNA, 50 nucleotides in length or less. Segments of RNA containing sequences of this type which exhibit IRES activity or DNA segments which can generate by transcription such RNA segments are useful in the construction of expression systems for proteins in recombinant production. Efficiency of production and assurance of translation can be enhanced by inclusion of these elements in expression systems. Such elements are also useful in screening systems for identifying trans-acting factors that assist in mediating translation.

The invention is directed to materials and methods which permit the identification of nucleotide sequences which represent internal ribosome entry site (IRES) elements. These elements are useful not only in construction of expression systems in a variety of host cells, but are also useful reagents to identify factors which are relevant to translation of RNA's in cells in general.

In one aspect, the invention method employs a bicistronic expression system of at least two modules, a first module which contains a first coding sequence whose translation is mediated by a 5' cap as a control and a second module which comprises a second coding sequence which has placed, upstream therefrom, a candidate IRES sequence. Typically, the candidate IRES sequence is 100 base pairs or less, more typically 75 base pairs or less, and preferably 50 base pairs or less. Thus, the systems useful in the invention will comprise a DNA which contains a promoter upstream of such a bicistronic system. Typically, the portion of the bicistronic system wherein the translation is cap mediated is placed downstream of the promoter but upstream of the portion of the bicistronic system wherein the translation is mediated by the candidate IRES. However, in an alternative configuration, the cap mediated translation module may be placed downstream of the test module.

Accordingly, in another aspect, the invention is directed to a bicistronic expression system as described above. In another aspect, the invention is directed to a method to identify a nucleotide sequence as an IRES element which method comprises culturing cells or a cell-free system with the expression system described above under conditions where the cap mediated translation occurs and assessing the expression of the module mediated by the putative IRES. Cells or cell-free systems which exhibit expression of the experimental module containing the candidate sequence are thus identified as containing an IRES element. The IRES element can then be recovered and sequenced and used in the manner described above.

In other aspects, the invention is directed to methods to use the IRES elements identified. These applications include methods to treat viral infections in cells, methods to identify trans-acting translation factors, and methods to alter cellular metabolism when said metabolism is controlled by proteins whose expression is mediated by an endogenous IRES element. The invention also includes compositions and kits containing them for use in these methods.

BRIEF DESCRIPTION OF THE DRAWINGS

FIGS. 2B-1–2B-3 shows a pilot experiment to establish screening conditions. The input pool, whose collective sequence is shown in the left panel, contained a mixture of plasmids in the ratio of 10000 pDF-e:1 pDF-E. After three rounds of screening for strong (pDF-E) IIRES elements, 700 positively selected clones were obtained; their collective sequence is shown in the right panel. In the middle panel is the collective sequence obtained when the sorting window was positioned so as to select poor (pDF-e) IRES elements. IRES positions 299–302, which have been mutated to create pDF-e, are shown in boldface; the sequence of pDF-e at these positions is 5'-AAAG-3', while the sequence of pDF-E is 5'-GCGA-3'. FIG. 2C shows the formulas of five nucleotide sequences identified by the method of the invention as potential IRES elements (SEQ ID NOS: 1–5).

FIGS. 3A–3H shows flow cytometric analysis of clones recovered from screen. Protoplasts were made from selected plasmids and fused to HEK293 cells. After 24 hours, cells were analyzed via flow cytometry for blue (Y-axis) and green (X-axis) fluorescence. PS2, PS3, and PS4 are positively selected clones, while NS I is a randomized 50-nt element that does not possess significant IRES activity. As a negative control, protoplasts from a control plasmid (pLuc-NI) that does not express fluorescent proteins was fused to HEK293 cells. Approiimately 10% of HEK293 cells were productively fused with protoplasts.

FIGS. 5A–5C shows IRES elements PS3 and PS4 compete with PV IRES-mediated translation in vitro.

MODES FOR CARRYING OUT THE INVENTION

Figure 1A:
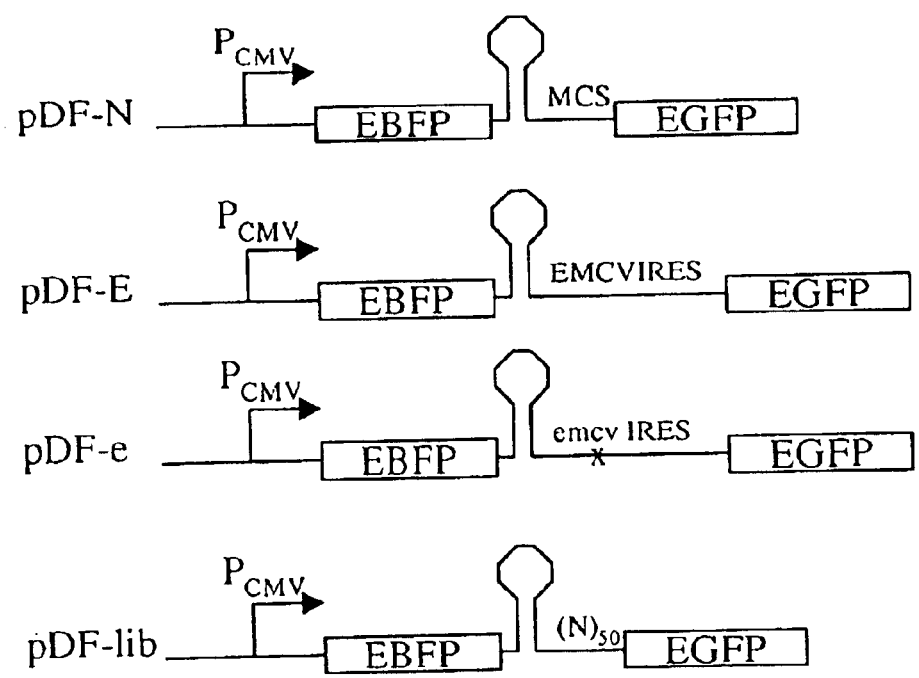
FIG. 1A shows diagrammatically plasmids containing the bicistronic system of the invention.

Illustrated below is one example of the bicistronic expression system of the invention which employs in vivo production of fluorescent proteins. In the illustrated system, a CMV promoter is used to drive transcription of both modules of the bicistronic system. The upstream module contains an element for cap mediated translation of a blue fluorescent protein; the downstream module of the bicistronic system contains the candidate nucleotide sequence upstream of the coding sequence for green fluorescent protein. By using FACS, cells which produce green fluorescent protein can be recovered through several rounds of sorting. The expression system is then isolated from these cells and sequenced to determine the sequence of the candidate IRES.

By screening a library of plasmids containing randomized sequences placed between two fluorescent reporters, 50 nucleotide-long stretches of RNA that promote IRES activity have been found. Two of these 50 nucleotide RNA's promote IRES-mediated translation both in vitro and in vivo, and do so in a context-independent manner in multiple cell types. Approximately $1\times10^6$ different sequences were screened, which is a very small percentage of the sequence space encompassed by a 50-nucleotide randomized region.

With a complex library (over three orders of magnitude larger than Robertson, et al., supra) and much rarer instances of positive IRES elements, 60–70% of the clones selected by the invention method contain the desired IRES activity. A large degree of enrichment is also observed. The presence of pDF-E was increased by more than 1,000-fold (see FIG. 2B) after three rounds of screening, in part due to use of protoplast fusion, rather than transfection. Significant enrichment of rare IRES elements occurred only when plasmids were introduced via protoplast fusion vs. transfection. The use of fluorescent reporters also offers advantages during selection, both cap-dependent translation of EBFP and IRES-mediated translation of EGFP in individual cells by flow cytometry can be monitored simultaneously. The levels of IRES activity that is selected are determined by choice of sorting windows.

Currently, viral IRES elements are often used in gene therapy applications. A retrovirus is typically engineered to contain a bicistronic construct encoding both a gene of interest that is translated via a cap-dependent mechanism and a reporter gene whose translation is directed by the viral IRES to ensure that both proteins are expressed in infected cells. One limitation of this approach is that viruses used to deliver genes are constrained by the amount of RNA that they can efficiently package into a virion, thus small synthetic IRES elements, which are at least 10 times smaller than the commonly used EMCV IRES element, allows for the incorporation of larger genes or multiple (3 or more) genes into a single retroviral vector. Randomly mutagenized viral IRES elements may be screened for attenuated or strengthened IRES activity, providing insight into RNA determinants of viral translation. Additionally, libraries of 5' untranslated regions of cellular mRNA's can be screened for IRES activity. Such an approach complements that of Johannes, G., et al., *RNA* (1998)4:1500–1513 in rapidly identifying many cellular IRES elements.

However, the fluorescent system described hereinbelow is merely illustrative. Any two reporter coding sequences can be used in the bicistronic system. Reporter genes such as chloramphenicol acetyl transferase (CAT), luciferase, horseradish peroxidase, and the like are well known and could be used. The cap-mediated translation provides a positive control, but could also be employed as an aid in affinity purification of the successfully expressing cells. For example, the cap-mediated expression might result in the production of a surface displayed receptor whose ligand could then be used to recover cells which have at least successfully resulted in cap-mediated translation. These cells can then be plated and assayed for production of the reporter protein associated with the candidate IRES.

The candidate IRES may be synthetic or may be derived from a natural source. As illustrated below, random sequences may be employed, or rational synthesis of the candidate IRES element may be used.

The bicistronic assay system of the invention results in the discovery of relatively short nucleotide sequences that function as IRES elements. Once a successful candidate is found, this IRES can be used in a number of ways.

First, by "IRES element" is meant both the RNA sequence included in the messenger and the DNA sequence which results in the RNA transcript. Thus, as used herein "IRES element" may refer either to DNA or RNA. The IRES element can be put into constructs where production of protein is required by inserting this element into the DNA which is transcribed into the mRNA to be translated for protein production. The IRES element is placed in the portion which results in the 5' untranslated region downstream of the promoter and upstream of the start codon. A variety of promoters, proteins, and the like can be employed.

As these elements operate in eukaryotic, typically vertebrate cells, promoters consistent with expression in these cells are typically used. Any suitable protein can be prepared aided by this upstream translation aid. Thus, in the simplest use of the IRES elements prepared by the method of the invention, they are simply used as a means to enhance protein production. The protein production by virtue of their inclusion may be enhanced by 50%, 100%, or even at a higher level, such as several fold or several tens of fold.

A second application of the IRES of the invention relates to use in identifying trans-acting factors which are important in translation events. Simple tests for binding of such factors to the IRES element identified by the invention could be used. Thus, the IRES may be, in one embodiment, attached to a solid support and contacted with cellular extracts wherein the cellular extracts have been generated using labeled precursors. Labeled proteins coupled to the immobilized IRES can then be detected, removed and identified. Alternatively, various cellular components can be produced in a phage display system which then is contacted with the immobilized IRES. Adsorbed phage are then eluted and amplified in order to identify the encoded protein by the nucleic acids contained in the phage. Any suitable method which measures the interaction between IRES and a candidate compound can be used; thus, candidate compounds as translation factors could also be tested individually for their ability to bind these sequences. Under these circumstances, the IRES would typically be prepared as an RNA, or the complement of the DNA from which the RNA is transcribed.

Still another use for the IRES of the invention is a method to inhibit the production of proteins whose production is mediated by an IRES element. Even though the competing IRES may be different from the IRES mediating protein production, the same trans-acting factors may be bound; the ability of the IRES of the invention to bind these factors in competition with the IRES element associated with the undesired protein will inhibit its production. Since many viral proteins are produced through IRES mediation, the IRES elements of the present invention are also antiviral agents. Other aspects of cellular metabolism could also be regulated using these nucleic acid molecules.

Although, as exemplified below, protoplast fusion is a preferred method to introduce the test systems of the invention into host cells, the invention includes the possibility of utilizing other methods such as transfection, retroviral transfer, electroporation, and lipid-induced transfection. Protoplast fusion is preferred because in some instances the efficiency of selecting strong IRES elements is enhanced thereby.

Thus, the following examples are intended to illustrate but not to limit the invention.

EXAMPLE 1

Construction of Bicistronic Systems to Screen for IRES

A series of bicistronic systems was constructed as shown in FIG. 1A. As shown schematically in the figure, all of the plasmids contain a CMV promoter upstream of the coding sequence for the blue fluorescent protein (EBFP). Downstream from the cistron encoding EBFP is a thermodynamically stable stem-loop structure and an additional cistron containing a nucleotide sequence encoding the green counterpart of the blue protein, EGFP. The pDF-N contains a multiple cloning site (MCS) for insertion of known or candidate IRES segments. As shown in FIG. 1A, pDF-E, which will be a positive control, contains the IRES from EMCV IRES; pDF-e contains a mutated form of this IRES which is no longer functional and will serve as a negative control. pDF-lib contains an insert of a random 50 nucleotide sequence which will be a candidate IRES. There is, of course, a multiplicity of pDF-lib plasmids which are used in the procedures to test IRES capability.

In more detail, EBFP was cloned between the HinDIII and NotI sites of pEGFP-N1 (Clontech), while the stem-loop (Negulescu, D., et al., *J. Biol. Chem.* (1998) 273:20109–20113) was placed between the Not1 and EcoRI sites. pDF-E is identical to pDF-N except that the EMCV IRES (from pIREShyg, Clontech) was inserted between the EcoRI and BamHI sites. pDF-e was made by inserting an EMCV IRES that was mutated by site-directed mutagenesis at positions 299–302, from 5'-GCGA-3' to 5'-AAAG-3', into pDF-N instead of wildtype EMCV IRES.

To create a randomized library for inclusion in pDF-lib, a PAGE-purified 50 nucleotide-long randomized oligonucleotide library (IDT) with sequence 5'-GCGCACTGATGAATTC-N$_{50}$-GGATCCTCAGACTCCG-3' (SEQ ID NO: 6) was obtained. The phosphoramidite ratio for random sequence DNA synthesis was normalized to account for differing coupling rates (Unrau, P. J., et al, *Nature* (1998) 395:260–263). The oligonucleotide pool was amplified by 10 cycles of PCR as described by Tuerk, C., *Methods in Mol. Biol.* (1997) 67:219–230, and the amplified DNA was cut with EcoRJ and BamHI and ligated to EcoRI-BamHI-digested pDF-N in ten separate reactions. Each ligation reaction was divided into two parts, and electroporated into DH5α cells. Each transformation yielded approximately 50,000 colonies; colonies were combined to yield a total pool of approximately 1×10$^6$ transformants.

The library of plasmids represented by the 1×10$^6$ transformants, termed pDF-lib, was analyzed for sequence diversity. Twenty-five individual clones were sequenced, and the nucleotide content of the approximately 1225 bases was found to be evenly distributed (25% G, 26% A, 24% T, 25% C). None of these clones had the same sequence. The lengths of the randomized inserts ranged from 48 nucleotides to 50 nucleotides, possibly due to incomplete separation of the oligonucleotide library during PAGE purification. To facilitate discussion, the library will be referred to as containing "50 nucleotide" insertions. One of the clones sequenced possessed, in its 50 nucleotide insert, a palindromic sequence recognized by the restriction enzyme KpnI, while another clone possessed a SmaI site. As an additional check for insert diversity in the library, one hundred other randomly selected clones were tested for the presence of KpnI or SmaI sites within their inserts and were found to be lacking both of these sites. It should be noted that because EcoRI and BamHI sites were used to construct the plasmid library, we expect that the sequences 5'-GAATTC-3' and 5'-GGATCC-3' will be underrepresented.

EXAMPLE 2

Insertion Into Cells

The constructs shown in FIG. 1A were placed into HEK cells through protoplast fusion. Protoplast fusion was performed essentially as described by Tan, R., et al., *Proc. Natl. Acad. Sci. USA* (1998) 95:4247–4252. Protoplasts from plasmid-containing DH-5α cultures were prepared as described (Sandri-Goldin R. M., et al., *Mol. Cell. Biol.* (1981) 1:743–752); conversion of rod-shaped bacteria to round protoplasts was monitored by phase-contrast microscopy. Protoplasts were slowly diluted with room temperature serum-free DMEM containing 10% sucrose and 10 mM MgCl$_2$, and held at room temperature for 15 min. Protoplasts (2–4 mL of suspension at approx. 1.5×10$^9$ protoplasts/mL) were added to HEK293 cells that had been grown to approximately 75% confluence in six-well plates, plates were centrifuged at 1650× g for 10 min at room temperature, and supernatants were removed. Two mL of room temperature 50% (wt/vol) PEG1500 was added to each well. After two min, PEG1500 was removed, cells were gently washed twice with 2 mL serum-free DMEM, and 4 mL DMEM containing 10% fetal bovine serum, penicillin and ampicillin was added. Cells were examined for fluorescence 24 hr later.

EXAMPLE 3

FACS Analysis of pDF-E and pDF-e

Transfected or protoplast-fused cells were resuspended 24 hr later at a concentration of 1–2×106 cells/mL in phosphate-buffered saline. Samples were analyzed or sorted by FACS using a dual-laser flow cytometer. An argon laser was used to excite cells at 488 nm and a 530±15 nm bandpass filter was used to detect EGFP expression, while a second laser tuned to 355 nm was used to excite EBFP, which was detected by a 424±22 nm collection filter. EGFP fluoresces at a much higher intensity than EBFP (approx. 30-fold higher), consistent with other reports. Both FACS analysis (5,000–10,000 cells per sample) and FACS sorting (2,500 cells/sec) were performed by using the UCLA Core Flow Cytometry Laboratory FACStar$^{plus}$ cell sorter (Becton Dickinson). FACS data were analyzed using CELLQUEST software.

Figures 1, 1B, 2:
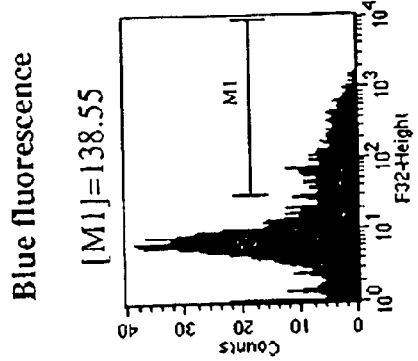
FIGS. 1B-1–1B-6 shows the flow cytometric (FACS) analysis of HEK293 cells transfected with pDF-E and pDF-e. Dot plots represent blue fluorescence (Y-axis) vs. green fluorescence (X-axis). Approximately 30% of the cells were transfected in this experiment. Region MI in the histogram plots represents transfected cells, and the mean fluorescence value of these cells is shown above each histogram.

Upon expression, the first cistron, EBFP, is translated via cap-dependent translation, while the second cistron, EGFP, should only be efficiently translated if a functional IRES element is present upstream. Twenty-four hours after transfection of the pDF plasmids into HEK293 cells, cells were analyzed for fluorescent protein expression via flow cytometry. As shown in FIG. 1B, the expression profiles of pDF-E transfected cells differ significantly from those cells transfected with pDF-e. Although the mean blue fluorescence, representative of cap-dependent translation, of cells transfected with pDF-E and pDF-e is almost identical, the mean green fluorescence of cells transfected with pDF-E is approximately six times greater than those cells transfected with pDF-e, indicating that pDF-E is a much stronger IRES than is pDF-e (FIG. 1B).

The fluorescent protein expression of pDF-e is very similar to that of pDF-N (data not shown for transfection, but see FIG. 3), which also contains a poor IRES element. Thus, flow cytometry allows distinguishing between plasmids containing poor IRES elements (pDF-e, pDF-N) and those containing strong IRES elements (pDF-E).

EXAMPLE 4

Suitability of Introduction of Plasmids into Protoplasts

A preferred method for introducing the test systems into host cells is through protoplast fusion. This example describes the advantages of this method. To compare the results using transfection with protoplast fusion, it was attempted to recover plasmids containing a strong IRES element after cotransfecting a large amount of plasmid DNA containing a poor IRES element (pDF-e) with a small amount of plasmid DNA encoding the strong IRES element (pDF-E).

HEK293 and Huh7 cells were seeded into 6-well or 96-well plates and allowed to reach 70% confluency. Transfection was performed by addition of a mixture containing 0.2–2.0 µg of DNA and either 0.5–3 µL Cytofectene (BioRad) or 1–4 µL Lipofectin and 1–8 µL Plus Reagent (Gibco-BRL) to cells. For fluorescence microscopy, 96-well plates were visualized directly on a Nikon Diaphot 200 inverted microscope using the UV-2A filter cube to detect EBFP and the GFP filter cube to detect EGFP expression.

Figure 2A:
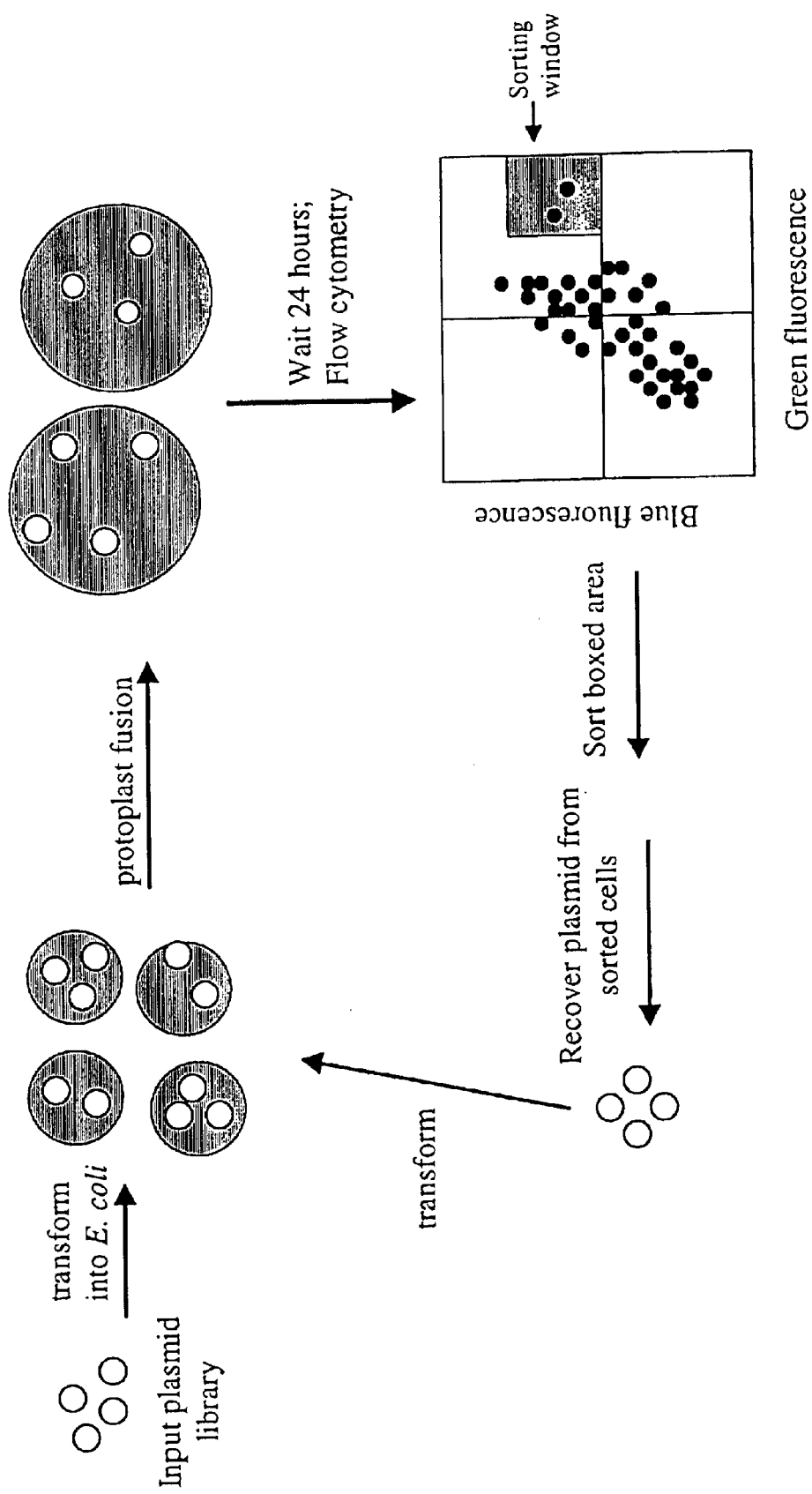
FIG. 2A shows the strategy for screening for IRES elements. The input plasmid library containing two fluorescent reporters is introduced into eukaryotic cells by protoplast fusion. Small shaded circles represent E. coli, and large shaded circles represent HEK293 cells. A suitable sorting window is used to isolate double-positive cells via FACS, and plasmids are extracted by alkaline lysis and electroporated into bacteria.

Plasmid DNA mixed in a ratio of $10^4$:1 (pDF-e: pDF-E) was transfected into HEK293 cells, and 24 hours later cells were subjected to FACS analysis, as described in Example 3, to recover cells that expressed significant levels of both EBFP and EGFP, indicative of those cells containing the pDF-E plasmid. Plasmid DNA was recovered from sorted cells, amplified in E. coli, and transfected into 293 cells for another round of screening, as shown in FIG. 2A. After three rounds of screening, 54 individual clones were sequenced; all possessed the pDF-e sequence, indicating that significant enrichment of strong IRES activity had not occurred.

The approximately 1,000 recovered colonies following the third round of screening were pooled and the pooled DNA was sequenced. No significant enrichment of the pDF-E sequence was noted (data not shown). Since it is well established that transfection of a combination of plasmids often leads to the delivery of all of them into the same cell, cells containing the pDF-E plasmid also contained large numbers of the pDF-e plasmid (due to the overabundance of pDF-e in the experiment), and that this background prevented successful enrichment of the population for pDF-E.

Protoplast fusion to deliver plasmids into HEK293 cells, is thus preferable as it results in near-clonal delivery of plasmids into cells. E. coli was transformed with plasmids encoding EBFP and EGFP in a 1:1 ratio, protoplasts were made and fused with 293 cells. Like Tan, et al., supra, the results showed that protoplast fusion is a near-clonal delivery process; fused cells expressed, for the most part, either EBFP or EGFP but not both. In contrast, cells cotransfected with plasmids expressing EBFP and EGFP in a 1:1 ratio expressed, for the most part, both EBFP and EGFP (data not shown). This protoplast fusion is a suitable method to deliver a library of plasmids in a near-clonal fashion into cells to ensure a low background during a screen.

As a pilot experiment, DNA encoding pDF-e and pDF-E in a $10^4$:1 ratio, were mixed and placed into protoplasts and fused with HEK293 cells. Positive cells were sorted 24 hours later via FACS. Plasmid DNA from positive cells (those expressing significant levels of both EBFP and EGFP) was isolated and transformed into E. coli, and protoplasts were again made and fused with 293 cells (FIG. 2A). After three rounds of selection, significant enrichment of pDF-E had occurred; 14 of the 20 clones (70%) sequenced had the pDF-E sequence (data not shown). In addition, the approximately 700 colonies recovered after three rounds of selection were pooled, and plasmid DNA was isolated and sequenced from this pool. A large percentage (>60%, as judged by quantitation of sequencing band intensities) of the clones recovered after three rounds of screening possessed the pDF-E sequence, 5'-GCGA-3', rather than the pDF-e sequence, 5'-AAAG-3', at EMCV IRES positions 299–302 (see FIG. 2B, "Positive Selection"). In contrast, sequencing of the input pool consisting of a pDF-e:pDF-E ratio of $10^4$:1, as well as of a population of clones selected for poor IRES activity (see FIG. 2B, "Input Pool" and "Negative Selection"), both displayed the population sequence 5'-AAAG-3' at positions 299–302. The screening method allows identification of rare, strong IRES elements under conditions that mimic a library screen.

EXAMPLE 5

Screening of a Randomized Library and Recovery of IRES Elements

As described above, protoplasts containing pDF-e, pDF-E; and pDF-lib were fused to HEK293 cells. After 24 hr, cells fused with pDF-E and pDF-e protoplasts were analyzed by FACS to establish a sorting window that would exclude most cells fused with pDF-e while including many of the cells fused with pDF-E. See FIG. 1B. Subsequently, approximately $3 \times 10^7$ cells fused with pDF-lib were sorted by FACS, and positive cells were collected and mixed with 50,000 unfused HEK293 cells. Plasmids were recovered by alkaline lysis essentially as described by Tan (supra), and electroporated into DH-5a cells; resulting colonies were used to make protoplasts for the next round of screening. See FIG. 2A. The cycle was repeated for three rounds, after which a significant proportion (>50%) of cells exhibited a similar fluorescence profile to cells fused with pDF-E.

Increasing numbers of EGFP-expressing cells were observed in each succeeding round (data not shown). Plasmids recovered after the third round of selection were individually transfected into HEK293 cells, and scored via fluorescence microscopy for EBFP and EGFP expression. Over 60% of the clones (97 out of 158 clones) recovered after three rounds of selection expressed significant levels of EGFP, indicating that successful enrichment of IRES activity had occurred. In comparison, none of the 142 clones assayed from the original randomized library, pDF-lib, expressed significant amounts of EGFP activity, though all clones expressed similar amounts of EBFP. Of the clones recovered after three rounds of selection that expressed significant levels of EGFP, five different sequences were found; these were named PS1 through PS5, and were subsequently analyzed by a variety of methods to determine whether they indeed encoded IRES activity. These sequences are shown in FIG. 2C.

Figures 1, 1B, 2, 3:
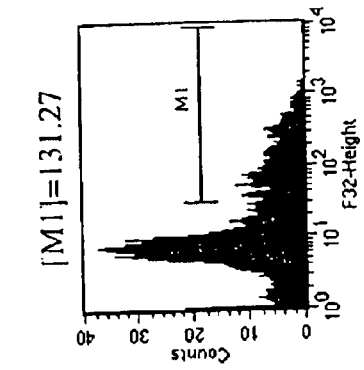

Protoplasts made from E. coli containing PS1 through PS5 were fused to HEK293 cells and analyzed by flow cytometry for expression of EBFP and EGFP. Shown in FIG. 3 are the results of such an experiment, in which the fluorescence profiles of three positively selected clones are displayed along with the profiles of pDF-e and pDF-E. The mean green fluorescence of all five of the positively selected clones was equal to or higher than that of pDF-E, and was 6–10 times higher than that of pDF-N or pDF-e, suggesting that the PS clones possess functional IRES elements that promote translation of the downstream cistron EGFP. Some of the cells receiving plasmids containing strong IRES elements appear to express EGFP but not EBFP (FIG. 3); this is most probably due to the fact that the intensity of EGFP fluorescence is approximately 30 times higher than that of EBFP. Therefore, cells receiving low numbers of plasmids containing strong IRES elements would express enough EGFP to be detected by flow cytometry, while the intensity of EBFP fluorescence would not be detectable.

Upon transfection of the pDF-ps plasmids into both HEK293 cells and Huh7 cells followed by flow cytometric analysis the mean green fluorescence of the PS clones was also 6–10 times higher than that of pDF-N or pDF-e, indicating that the activity of these IRES elements is not restricted to a single cell type or to a particular method of plasmid delivery into mammalian cells.

EXAMPLE 6

Context Dependence of Selected IRES Elements

To determine whether the PS elements could function as IRES elements in different contexts, in vitro translation studies were performed. HeLa extracts were prepared as described previously, and in vitro translation was performed under standard conditions (Das, S., et al., *J. Virol.* (1994) 68:7200–7211). Briefly, 40 µg of HeLa translation extract was incubated at 37° C. for 1 hr with 0.5 to 2.0 µg of template RNA prepared by standard in vitro transcription before analysis by SDS-polyacrylamide gel electrophoresis. In competitive translation experiments, a 2- to 4-fold molar excess of competitor RNA was pre-incubated with HeLa extract and all other components necessary for translation at 37° C. for 10 min before the template RNA was added. UV-crosslinking experiments were also performed as described by Das (supra); $^{32}$P-labeled RNA was incubated with HeLa translation extract for 10 min before being subjected to short-wave UV irradiation. After RNase treatment, samples were analyzed by SDS-polyacrylamide gel electrophoresis. In competitive UV-crosslinking experiments, a 100- to 250-fold molar excess of competitor RNA was preincubated with HeLa extract before addition of $^{32}$P-labeled RNA.

Figure 4A:
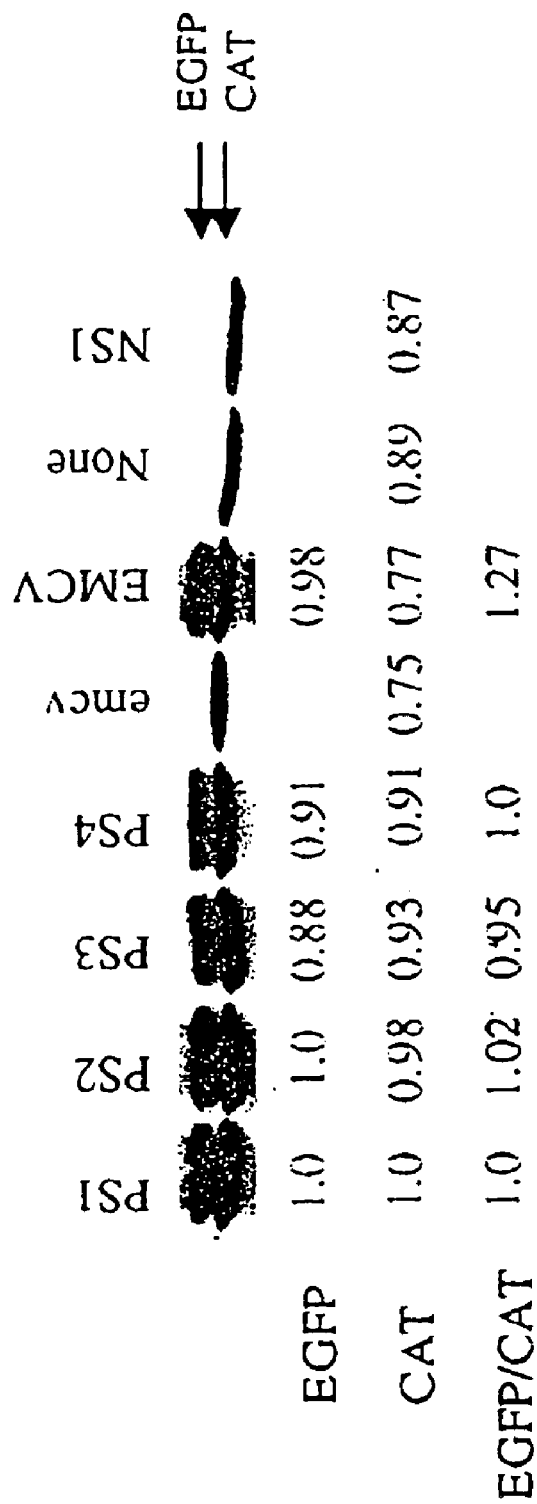
FIG. 4A shows effects of removal of upstream cistron on IRES activity of recovered elements. Two ug of uncapped monocistronic RNA's consisting of the stem-loop structure followed by either the 50-nt sequences (PS 1–4, NS 1), no intervening sequence (None), the EMCV IRES variant (EMCV), or its mutant form (emcv) were use a in in vitro HeLa translation reactions. Each reaction also contained 500 ng of capped CAT RNA for comparative purposes, and the results of densitometric analysis of bands representing translated proteins, normalized to levels of translation in the PS1 reaction, is shown below. Translation of EGFP directed by NS1, None, and emcv were undetectable by densitometric quantitation.

The upstream cistron, EBFP, was eliminated, leaving the stem-loop structure upstream of the IRES element followed by EGFP. (See FIG. 1A.) Uncapped mRNA was transcribed and translated in vitro, and the results are depicted in FIG. 4A. The four PS elements shown in FIG. 4A, as well as PS5, all promote levels of EGFP translation that are significantly higher than the virtually undetectable translation levels directed by a randomized element that does not possess significant IRES activity (NS1), or by a construct in which there are no intervening nucleotides between the stem-loop and EGFP (None).

In vitro transcribed and 5'-capped monocistronic CAT RNA was added to each reaction in order to compare translation directed by the various PS elements with cap-dependent translation. Quantitation of bands in FIG. 4A indicates that levels of EGFP translation directed by the PS elements are similar to that directed by the EMCV IRES variant. Addition of the EMCV IRES to in vitro translation reactions is known to inhibit capped mRNA translation, presumably by the ability of the J-K region to sequester cellular factors needed for translation; such an effect is also seen here with the mutant form of the EMCV IRES, which also contains the J-K region.

Similar results to those seen in FIG. 4A were obtained in in vitro translation reactions where both the upstream cistron and the stem-loop were removed, leaving a monocistronic construct consisting of the IRES followed by EGFP (data not shown). These results show the PS elements found in the bicistronic screen also function as IRES elements in a monocistronic context in the absence of upstream sequences.

EXAMPLE 7

Effect of the Encoded Message on Translation

Figure 4B:
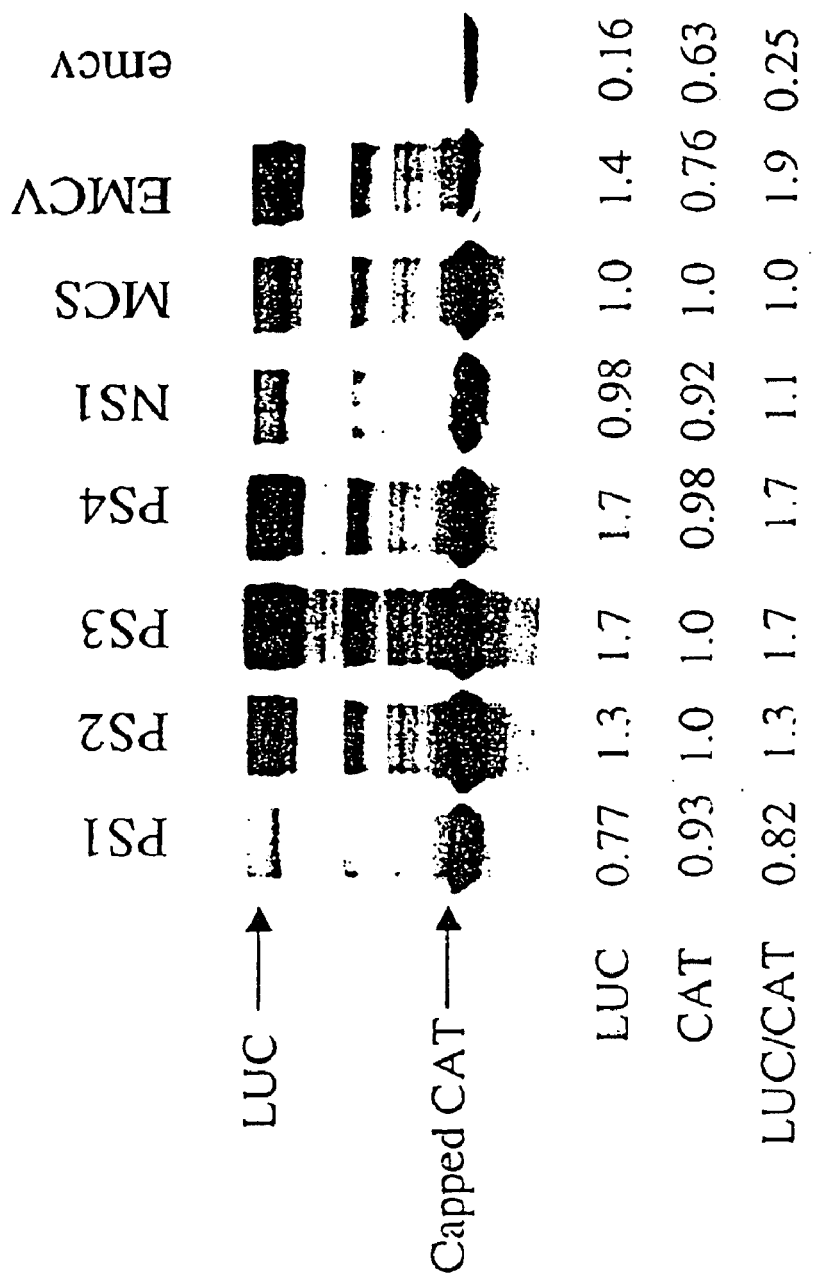
FIG. 4B shows context-independence of elements PS3 and PS4. Two $\mu$g of uncapped monocistronic RNA's consisting of either the 50-nt sequences (PS1–4, NS1), the multiple cloning site from pDF-N (MCS), the EMCV IRES from pDF-E (EMCV), or the mutant EMCV IRES from pDF-e (emcv) upstream of firefly luciferase (Luc) were used in in vitro HeLa translation reactions. Each reaction also contained 500 ng of capped CAT RNA, and densitometric analysis of proteins is shown below.
Figure 4C:
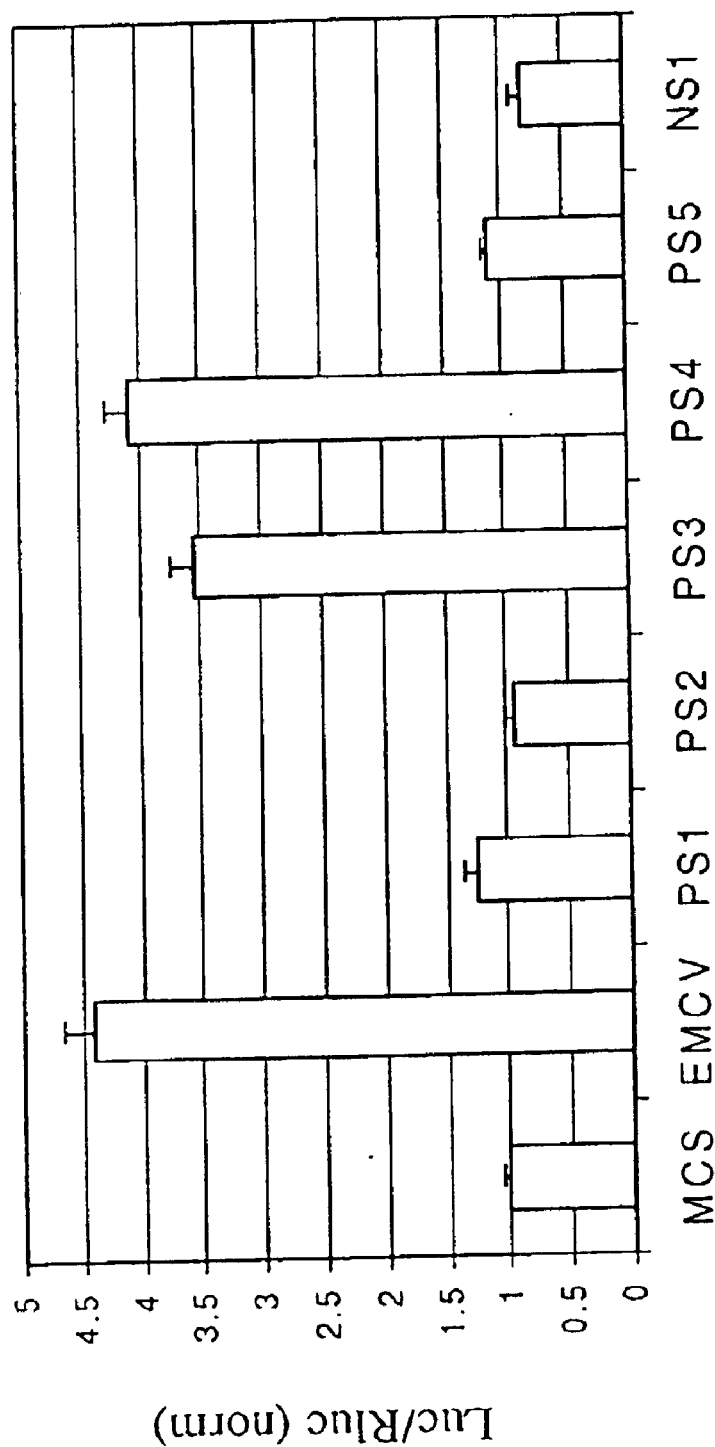
FIG. 4C shows PS3 and PS4 possess context-independent IRES activity in vivo. The 50-nt elements, MCS, or EMCV IRES were placed in a bicistronic plasmid between Renilla luciferase (Rluc) and firefly luciferase (Luc). Twenty-four hours after transfection into HEK293 cells, cells were analyzed for Luc and Rluc activity. The Luc/Rluc ratios, normalized to that found in cells transfected with the MCS-containing plasmid, are shown. Experiment was performed two separate times in triplicate.
Figure 6A:
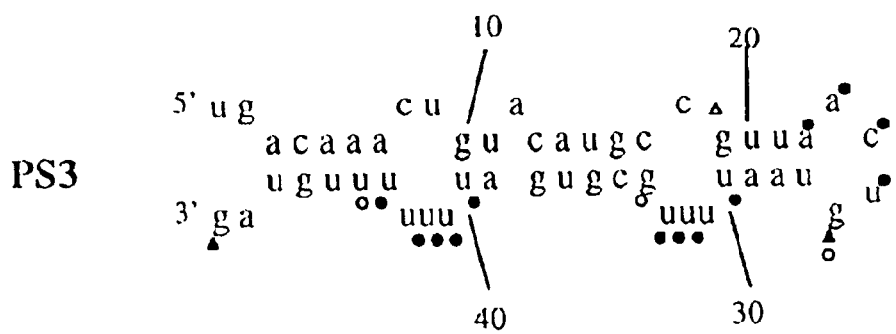
FIGS. 6A–6B shows proposed secondary structures of PS3 and PS4 with an enzymatic digestion map. Triangles represent nucleotides reactive to RNase T1 and circles mark nucleotides reactive to nuclease S1. Solid symbols represent strong reactivities, while open symbols represent weak reactivities. RNase VI, which we have previously used to identify basepaired regions of other RNA's, is not currently available to the scientific community and hence was not used in this study.
Figure 6B:
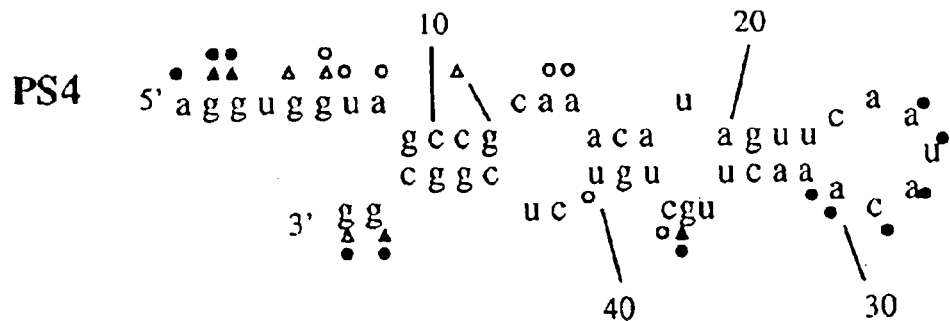

This example explores the effect of the nature of the downstream cistron on the ability of the PS elements to direct IRES-mediated translation. Monocistronic RNA consisting of the IRES element followed by the firefly luciferase gene (Luc) rather than EGFP was prepared in vitro and translated in HeLa extracts, as described above. As shown in FIG. 4B, both PS1 and PS2 lost IRES activity when placed before Luc, as did PS5 (data not shown). On the other hand, elements PS3 and PS4 were still able to significantly direct IRES-mediated translation when placed before Luc. Because the bands corresponding to Luc were somewhat diffuse in FIG. 4B, the results were confirmed using Luc activity via a luminometer. In this case also, addition of the EMCV IRES repressed cap-dependent translation of CAT (compare FIG. 4B with FIG. 4A). In addition, bicistronic plasmids consisting of the reporter genes *Renilla* luciferase (Rluc) and Luc separated by the PS elements (analogous to FIG. 1A) were constructed and called pDL-ps. For dual luciferase assays, 6-well plates were washed in PBS(−) and resuspended in Cell Culture Lysis Buffer (Promega) before analysis of Luc and Rluc expression by the Promega Dual Luciferase System on a Monolight 2010 Luminometer (Analytical Luminescence Laboratory). Upon transfection of pDL-ps plasmids into HEK293 cells, PS3 and PS4 again show levels of IRES activity comparable to that of the EMCV IRES, as assayed by Luc/Rluc ratio (FIG. 4C). Thus, the selected elements PS3 and PS4 can promote IRES-mediated translation from bicistronic constructs in vivo and from monocistronic constructs in vitro in a context-independent manner.

EXAMPLE 8

Ability of IRES Segments to Inhibit Native IRES Translation

Figures 1, 1B, 2, 3, 4, 5:
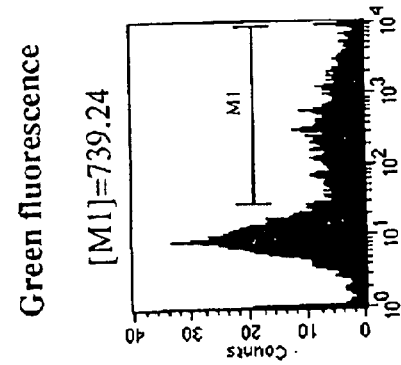

The in vitro translation system of Example 6 was used to test the ability of PS3 and PS4 to inhibit translation mediated by other IRES elements. The results of a competitive in vitro translation experiment in which Luc translation is directed by the PV IRES while CAT is made by cap-dependent mechanisms as shown in FIG. 5A. Pre-incubation of elements PS3 and PS4 in these translation reactions led to a decrease in PV IRES-mediated translation of Luc, while cap-dependent translation of CAT is not significantly affected (FIG. 5A, lanes 4–7). A four-fold, but not a two-fold molar excess of PS3 and PS4 reduced Luc translation significantly (FIG. 5A and data not shown). However, HCV and EMCV mediated translation were not inhibited. Addition of the poor IRES NS I at four-fold molar excess (FIG. 5A, lane 8) did not affect either PV IRES-mediated or cap-dependent translation. Pre-incubation with PV IRES as the competitor (FIG. 5A, lanes 2 and 3) led to a decrease in both PV IRES-directed Luc translation and cap-dependent translation. This may be due to the binding by PV IRES of general translation factors also required for cap-dependent translation.

EXAMPLE 9

Binding Profiles

The protein binding profiles of PS3 and PS4 were determined by UV-crosslinking these $^{32}$P-labeled PS3 and PS4 to proteins in HeLa translation extract. As shown in FIG. 5B, PS3 and PS4 bind many proteins of the same apparent molecular weight as does the PV IRES. In particular, polypeptides of apparent molecular weight 80 kDa, 75 kDa, 66 kDa, 50 kDa and 35 kDa are bound by PS3, PS4, and PV IRES (see FIG. 5B, lanes 2–4). Also, a protein of apparent molecular weight 38 kDa was bound very strongly by PS3;

a protein of similar apparent weight was also bound by the PV IRES (FIG. 5B, lanes 2 and 3).

The binding profile of a 50-nucleotide RNA that does not promote significant IRES-mediated translation, NS1, is included for comparison. As can be seen in FIG. 5B (lane 5), there is no significant similarity between the protein binding profile of NS I and those of PV IRES, PS3, and PS4. A competitive UV-crosslinking assay, in which unlabeled PS3 and PS4 were pre-incubated with HeLa extract before UV-crosslinking with $^{32}$P-labeled PV IRES RNA was performed to determine whether the identities of some of the proteins bound by PS3 and PS4 are the same as those bound by the PV IRES. As seen in FIG. 5C, PS3 and PS4 compete significantly for certain proteins that are bound by the PV IRES. In particular, PS3, which bound a 38 kDa protein very strongly (FIG. 5B), efficiently competes out p38 binding by PV IRES (FIG. 5C, lanes 4 and 5). PS4 appears to compete for the binding of a wider range of PV IRES-bound proteins, including p80, p50, and, to a lesser extent, p38 (FIG. 5C, lane 7). The nonspecific RNA (NS 1) was able to compete with PV IRES binding to some extent (FIG. 5C, lane 8) at the highest concentration tested. These data suggest that PS3 and PS4 may employ some of the same trans-acting factors as PV to efficiently direct IRES-mediated translation.

EXAMPLE 10

Determination of Secondary Structures of PS3 and PS4

Close inspection of the sequences of PS3 and PS4 (see FIG. 2C) revealed no significant homology to each other or to known viral or cellular IRES elements, except for the presence of a polypyrimidine tract at the 3' end of PS3. Also, no regions of potential complementarity between these IRES elements and 18S ribosomal RNA were noted, suggesting no obvious mechanism by which these elements can directly bind 18S rRNA through base-pairing interactions. Since it is hypothesized that RNA structure plays an important role in IRES activity, PS3 and PS4 were further characterized by determining their secondary structures using a combination of enzymatic cleavage analysis and free energy minimization modeling.

Structural analysis of RNA, which involved free energy minimization modeling and nuclease probing, was performed essentially as described by Venkatesan, A., et al., Nuc. Acids Res. (1999) 27:562–572. Secondary structure predictions, were obtained using the RNA folding program MFOLD; for each RNA, all structures within 10% of the minimum predicted free energy were retained as possible candidates. Nuclease probing was performed by equilibrating RNA's by heating to 65° C. for 5 min and slow cooling to 37° C. Digestions with nuclease S1 (Promega) and RNase T1 (Boehringer Mannheim) were performed in an RNA buffer (50 mM sodium acetate, pH 4.5, 280 mM NaCl, and 4.5 mM ZnSO$_4$) at 37° C. for 10 min, and primer extension with radiolabeled oligonucleotide primers was performed essentially as described by Stem, S., et al., Meth. Enzymol. (1988) 164:481. For position markers, sequencing ladders were generated from plasmid DNA using the same primers and a Sequenase v.2.0 kit (US Biochemicals), and all samples were analyzed via denaturing polyacrylamide gel electrophoresis.

Figures 1, 1B, 2, 3, 4, 5, 6:
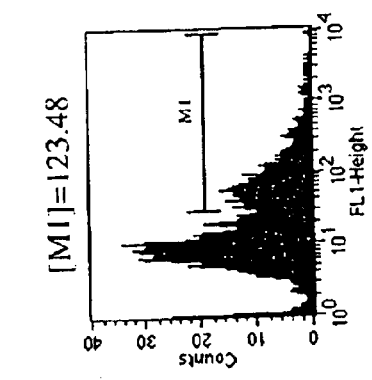
Figures 1, 1B:
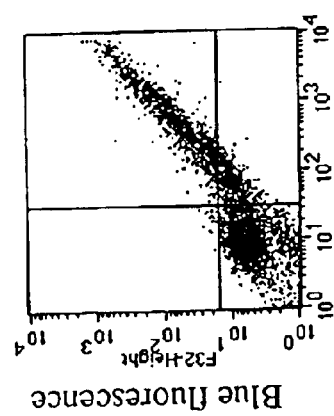
Figures 1, 1B, 2, 3, 4:
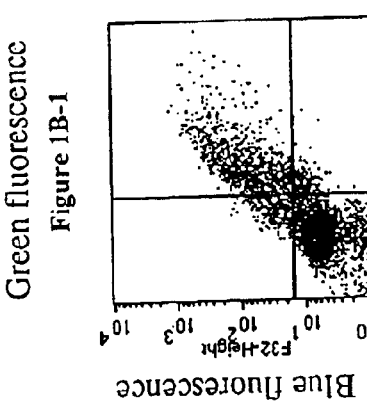

Depicted in FIG. 6 are the proposed structures of PS3 and PS4 based on fitting the results of nuclease cleavage of the PS3 and PS4 RNA's with MFOLD-predicted secondary structures (Zuker, M., Science (1989) 244:48–52). The proposed structure of PS3 is the one predicted by the MFOLD algorithm to have the lowest free energy (−6.9 kcal/mol), while that of PS4 is the one predicted to have the second lowest free energy 7.7 kcal/mol). The MFOLD-predicted structure for PS4 with the lowest free energy (−8.4 kcal/mol) was excluded based on nuclease cleavage pattern; for example, strong RNase T1 cleavage of nucleotide 36 and almost complete protection from cleavage of nucleotide 44 was observed. This is compatible with the structure of PS4 displayed in FIG. 6 but not with the lowest free energy structure (data not shown). No obvious secondary structural homology was noted between these two small IRES elements and other known viral IRES elements.

It has been proposed that a number of cellular IRES elements contain a "Y-type" stem-loop motif that may be involved in their function. However, this motif is also absent in the secondary structures of PS3 and PS4.

It is possible that PS 1, PS2, and PS5 did not function as context-independent IRES elements because their secondary structures were altered when the downstream reporter was changed from EGFP to Luc; or that there are sequences within EGFP contributing to the IRES activity of these three elements.

As set forth above, the IRES of picornaviruses consist of approximately 450 nucleotides that are highly structured and possess, at the 3' end, a conserved UUUC motif followed by a polypyrimidine tract, a G-poor spacer, and an AUG triplet. None of the PS1–PS5 possess the UUUC motif, two have a polypyrimidine tract at the 3' end, and none are notably lacking in G residues. Comparison of the sequences of PS1–PS5 elements to rRNA database sequences did not reveal any significant stretches of 9 nucleotides or longer which are complementary to 18S rRNA. Structural analyses of PS3 and PS4 also indicate that no Y-type stem-loop motif is present; rather, the structures consist of alternating stems and bulges. Alignment of the PS1–PS5 with GeneBank sequences revealed no significant homologies.

However, based on UV-crosslinking and in vitro translation studies, PS3 and PS4 interact with cellular proteins that are also bound by the PV IRES.

What is claimed is:

1. A method to identify an IRES element which method comprises providing a bicistronic expression system which comprises, in operable linkage with a promoter, first nucleotide sequence encoding a first reporter protein and a cap sequence for mediation of translation of said first reporter protein and a second nucleotide sequence encoding a second reporter protein wherein a candidate IRES element is upstream of said second nucleotide sequence, wherein said expression system is made intracellular by protoplast fusion;

culturing said intracellular expression system under conditions wherein said first nucleotide sequence is transcribed and translated into protein; and determining the presence or amount of production of said second reporter protein, wherein the presence or amount of said second reporter protein indicates that the candidate IRES element performs as an IRES element.

2. The method of claim 1, wherein said first and second reporter proteins are fluorescent proteins having distinguishable fluorescence.

3. The method of claim 2, wherein said determining is through FACS analysis.

4. The method of claim 1, wherein the candidate IRES element is a randomized nucleotide sequence of <100 nucleotides.

5. A method to control viral infection in a cell which method comprises contacting said cell with an IRES element identified by the method of claim 1, under conditions wherein said IRES element inhibits production of viral proteins.

6. A method to identify a trans-acting translation factor which method comprises assessing the ability of a candidate factor to interact with an IRES element identified by the method of claim 1.

7. The method of claim 6, wherein said candidate is included in a cellular extract.

8. A method to regulate cellular metabolism which method comprises contacting a cell with an IRES element identified by the method of claim 1 under conditions wherein said IRES element is exposed to trans-acting factors necessary for said intracellular metabolism.

9. A nucleic acid molecule comprising an IRES element, wherein said IRES element is selected from the group consisting of SEQ ID NO:1, SEQ ID NO:2, SEQ ID NO:3, SEQ ID NO:4, and SEQ ID NO:5.

10. A nucleic acid molecule of claim 9, wherein said IRES element is SEQ ID NO:3 or SEQ ID NO:4.

11. A method to control viral infection in a cell which method comprises contacting said cell with a nucleic acid molecule comprising an IRES element of claim 9, under conditions wherein said IRES element inhibits production of viral proteins.

12. A method to regulate cellular metabolism which method comprises contacting a cell with a nucleic acid molecule comprising an IRES element of claim 9 under conditions wherein said IRES element is exposed to trans-acting factors necessary for said intracellular metabolism.

13. A method to identify a trans-acting translation factor which method comprises assessing the ability of a candidate factor to interact with an IRES element, wherein said IRES element is selected from the group consisting of SEQ ID NO:1, SEQ ID NO:2, SEQ ID NO:3, SEQ ID NO:4, and SEQ ID NO:5.

14. The method of claim 13, wherein said candidate is included in a cellular extract.

* * * * *

UNITED STATES PATENT AND TRADEMARK OFFICE
CERTIFICATE OF CORRECTION

PATENT NO. : 6,833,254 B2
DATED : December 21, 2004
INVENTOR(S) : Asim Dasgupta et al.

It is certified that error appears in the above-identified patent and that said Letters Patent is hereby corrected as shown below:

Column 1,
Line 10, please insert the following paragraph:

-- ACKNOWLEDGEMENT OF GOVERNMENT SUPPORT

This invention was made with Government support under Grant No. AI45733, awarded by the National Institutes of Health. The Government has certain rights in this invention. --

Signed and Sealed this

Third Day of May, 2005

JON W. DUDAS
*Director of the United States Patent and Trademark Office*

SEQUENCE LISTING

<160> NUMBER OF SEQ ID NOS: 6

<210> SEQ ID NO 1
<211> LENGTH: 48
<212> TYPE: DNA
<213> ORGANISM: Artificial Sequence
<220> FEATURE:
<223> OTHER INFORMATION: Potential IRES elements -continued

```
<220> FEATURE:
<223> OTHER INFORMATION: Potential IRES elements

<400> SEQUENCE: 1
cacagtacgt aagcttaagc taagcgtaga taagggtata tttttgcg          48

<210> SEQ ID NO 2
<211> LENGTH: 50
<212> TYPE: DNA
<213> ORGANISM: Artificial Sequence
<220> FEATURE:
<223> OTHER INFORMATION: Potential IRES elements

<400> SEQUENCE: 2
gaaatagcta tcctccatca ctgcaccgag actacggttg cgcgtgtcgt         50

<210> SEQ ID NO 3
<211> LENGTH: 49
<212> TYPE: DNA
<213> ORGANISM: Artificial Sequence
<220> FEATURE:
<223> OTHER INFORMATION: Potential IRES elements

<400> SEQUENCE: 3
tgacaaactg tacatgccgt taactgtaat tttgcgtgat tttttttgta         49

<210> SEQ ID NO 4
<211> LENGTH: 48
<212> TYPE: DNA
<213> ORGANISM: Artificial Sequence
<220> FEATURE:
<223> OTHER INFORMATION: Potential IRES elements

<400> SEQUENCE: 4
aggtggtagc cgcaaacata gttcaataca aacttgctgt ctcggcgg          48

<210> SEQ ID NO 5
<211> LENGTH: 50
<212> TYPE: DNA
<213> ORGANISM: Artificial Sequence
<220> FEATURE:
<223> OTHER INFORMATION: Potential IRES elements

<400> SEQUENCE: 5
aggcagtata atcagttccc acatagaaaa ccaggactgt atcaaagtgt         50

<210> SEQ ID NO 6
<211> LENGTH: 82
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (1)...(82)
<223> OTHER INFORMATION: n = A,T,C or G

<400> SEQUENCE: 6
gcgcactgat gaattcnnnn nnnnnnnnnn nnnnnnnnn nnnnnnnnn nnnnnnnnnn    60 nnnnnnggat cctcagactc cg                                          82
```